(12) United States Patent
Rose

(10) Patent No.: US 6,514,508 B1
(45) Date of Patent: Feb. 4, 2003

(54) ITCH REDUCING DEVICE AND METHOD

(76) Inventor: Jeffrey Rose, 8531 Ridge Rd., Seminole, FL (US) 33772

( * ) Notice: Subject to any disclaimer, the term of this patent is extended or adjusted under 35 U.S.C. 154(b) by 0 days.

(21) Appl. No.: 09/939,037

(22) Filed: Aug. 24, 2001

(51) Int. Cl.[7] .............................................. A01N 25/34
(52) U.S. Cl. ...................... 424/404; 424/402; 424/403; 514/939
(58) Field of Search ................................ 424/404, 402, 424/443; 514/939

(56) References Cited

U.S. PATENT DOCUMENTS

| | | |
|---|---|---|
| 4,910,020 A | 3/1990 | Samour |
| D342,025 S | 12/1993 | Abraben et al. |
| 5,613,609 A | 3/1997 | Hamilton et al. |
| 5,863,663 A * | 1/1999 | Mackey et al. ............ 428/484 |
| 5,888,984 A | 3/1999 | Brown |
| 6,071,962 A * | 6/2000 | Ptchelintsev et al. ....... 514/513 |
| 6,110,488 A | 8/2000 | Hoffmann |
| 6,120,792 A | 9/2000 | Juni |
| 6,305,531 B1 * | 10/2001 | Wilkman .................... 206/210 |

OTHER PUBLICATIONS

Remington: The Science and Practice of Pharmacy, Acetone, p. 1404, vol. II, 1995.*
Goodman & Gilman's The Pharmacological Basis of Therapeutics, Tolnaftate, p. 1187, 19th Edition, 1996.*

* cited by examiner

*Primary Examiner*—Thurman K. Page
*Assistant Examiner*—Robert M. Joynes

(57) ABSTRACT

An itch reducing device and method for reducing the itch of a mosquito bite. The itch reducing device and method includes a pad comprising an absorbent material. An itch reducing ointment generally saturates the pad. A package has an upper layer and a lower layer joined at perimeter edges of the upper and lower layers. The pad is positioned in the package for storage until needed.

5 Claims, 1 Drawing Sheet

ITCH REDUCING DEVICE AND METHOD

BACKGROUND OF THE INVENTION

1. Field of the Invention

The present invention relates to itch reducing ointments and more particularly pertains to a new itch reducing device and method for reducing the itch of a mosquito bite.

2. Description of the Prior Art

The use of itch reducing ointments is known in the prior art. More specifically, itch reducing ointments heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U.S. Pat. Nos. 5,613,609; 4,910,020; 5,888,984; 6,120,792; 6,110,488; and U.S. Des. Pat. No. 342,025.

While these devices fulfill their respective, particular objectives and requirements, the aforementioned patents do not disclose a new itch reducing device and method. The inventive device includes a pad comprising an absorbent material. An itch reducing ointment generally saturates the pad. A package has an upper layer and a lower layer joined at perimeter edges of the upper and lower layers. The pad is positioned in the package for storage until needed.

In these respects, the itch reducing device and method according to the present invention substantially departs from the conventional concepts and designs of the prior art, and in so doing provides an apparatus primarily developed for the purpose of reducing the itch of a mosquito bite.

SUMMARY OF THE INVENTION

In view of the foregoing disadvantages inherent in the known types of itch reducing ointments now present in the prior art, the present invention provides a new itch reducing device and method construction wherein the same can be utilized for reducing the itch of a mosquito bite.

The general purpose of the present invention, which will be described subsequently in greater detail, is to provide a new itch reducing device and method apparatus and method which has many of the advantages of the itch reducing ointments mentioned heretofore and many novel features that result in a new itch reducing device and method which is not anticipated, rendered obvious, suggested, or even implied by any of the prior art itch reducing ointments, either alone or in any combination thereof.

To attain this, the present invention generally comprises a pad comprising an absorbent material. An itch reducing ointment generally saturates the pad. A package has an upper layer and a lower layer joined at perimeter edges of the upper and lower layers. The pad is positioned in the package for storage until needed.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new itch reducing device and method apparatus and method which has many of the advantages of the itch reducing ointments mentioned heretofore and many novel features that result in a new itch reducing device and method which is not anticipated, rendered obvious, suggested, or even implied by any of the prior art itch reducing ointments, either alone or in any combination thereof.

It is another object of the present invention to provide a new itch reducing device and method which may be easily and efficiently manufactured and marketed.

It is a further object of the present invention to provide a new itch reducing device and method which is of a durable and reliable construction.

An even further object of the present invention is to provide a new itch reducing device and method which is susceptible of a low cost of manufacture with regard to both materials and labor, and which accordingly is then susceptible of low prices of sale to the consuming public, thereby making such itch reducing device and method economically available to the buying public.

Still yet another object of the present invention is to provide a new itch reducing device and method which provides in the apparatuses and methods of the prior art some of the advantages thereof, while simultaneously overcoming some of the disadvantages normally associated therewith.

Still another object of the present invention is to provide a new itch reducing device and method for reducing the itch of a mosquito bite.

Yet another object of the present invention is to provide a new itch reducing device and method which includes a pad comprising an absorbent material. An itch reducing ointment generally saturates the pad. A package has an upper layer and a lower layer joined at perimeter edges of the upper and lower layers. The pad is positioned in the package for storage until needed.

Still yet another object of the present invention is to provide a new itch reducing device and method that allows a user to store and transport, in a convenient manner, an itch reducing ointment which is easily applied to the skin.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
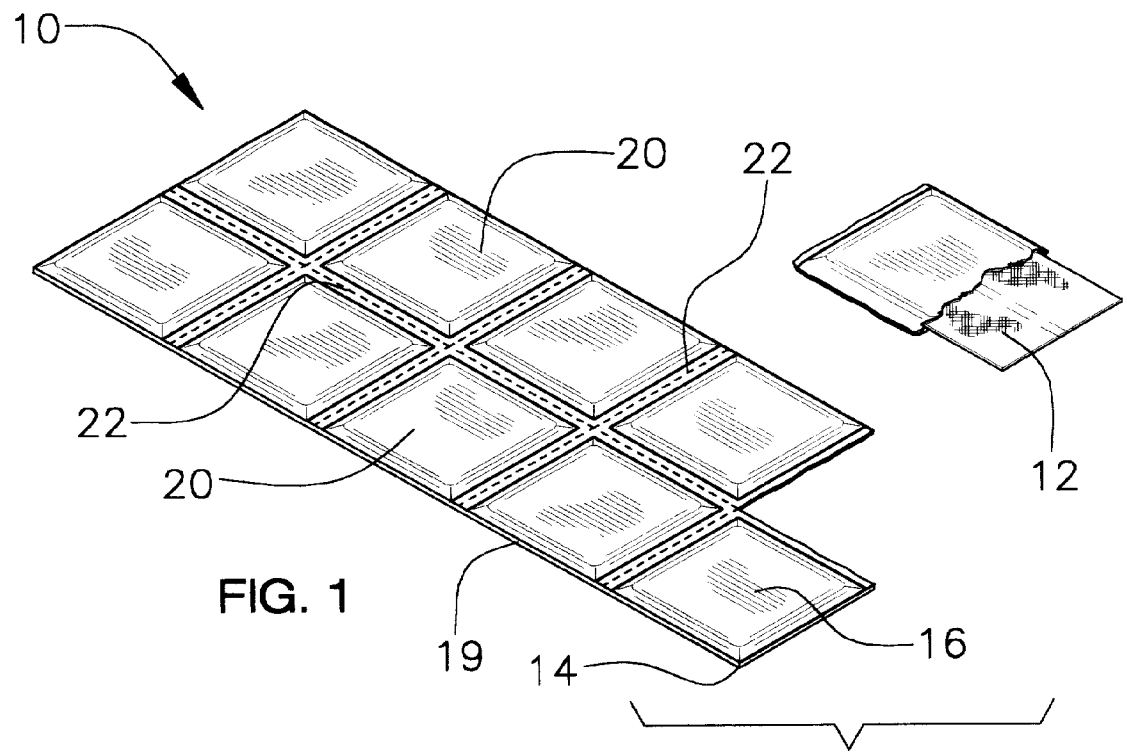
FIG. 1 is a schematic perspective view of a new itch reducing device and method according to the present invention.
Figure 2:
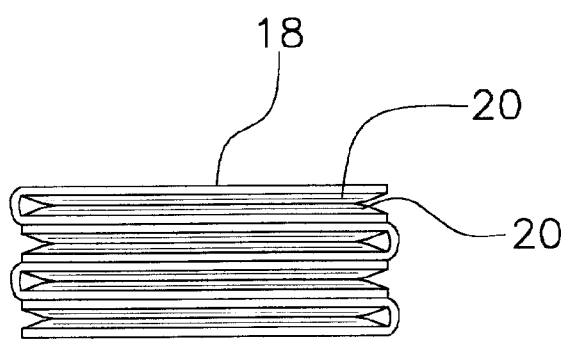
FIG. 2 is a schematic side view of the present invention.

With reference now to the drawings, and in particular to FIGS. 1 and 2 thereof, a new itch reducing device and method embodying the principles and concepts of the present invention and generally designated by the reference numeral 10 will be described.

As best illustrated in FIGS. 1 and 2, the itch reducing device and method 10 generally comprises a plurality of pads 12. Each of the pads 12 comprises an absorbent material. Ideally, the absorbent material comprising a cotton material.

An itch reducing ointment saturates each of the pads 12. The ointment preferably comprises tolnaftate, acetone, tocopheryl acetate, propylene glycol, and water. The preferred embodiment contains between 1% and 2% of tolnaftate by volume. Such a mixture may be obtained from PPR, Inc. 74 20th Street, Brooklyn, N.Y. 11232.

A package 14 has an upper layer 16 and a lower layer 18 joined at perimeter edges 19 of the upper and lower layers. The package 14 is segregated into a plurality of discreet packets 20. A plurality of perforations 22 extends through the package along lines generally diving the packets 20 from each other. This allows for tearing the packets 20 apart from each other and for easy storage as shown in FIG. 2. Each of the pads 12 is positioned in one of the packets 20. Each the packets 20 comprises a plastic material.

In use, when a person is bit by an insect, particularly a mosquito, one of the packets 20 it torn away from the package 14 along the perforations 22. The packet 20 is torn open as depicted in FIG. 1 and the pad 12 removed. The pad 12 is rubbed on the bite area such that the ointment is in contact with the bite area. The ointment reduces or eliminates the itch of bite.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An itch reducing device for reducing the itch of an insect bite, said device comprising:

a pads comprising an absorbent material;

an itch reducing ointment generally saturating said pad;

a package having an upper layer and a lower layer joined at perimeter edges of the upper and lower layers, said pad being positioned in said package; and wherein said ointment comprises tolnaftate, acetone, tocopheryl acetate, propylene glycol, and water, wherein said tolnaftate is between 1% and 2% by volume of the ointment.

2. The itch reducing device as in claim 1, wherein said absorbent material comprises a cotton material.

3. The itch reducing device as in claim 1, wherein said pads comprise a plurality of pads saturated with said ointment, said package being segregated into a plurality of discreet packets, a plurality of perforations extending through said package along lines dividing said packets from each other, each of said pads being positioned in one of said packets.

4. An itch reducing device for reducing the itch of an insect bite, said device comprising:

a plurality of pads, each of said pads comprising an absorbent material, said absorbent material comprising a cotton material;

an itch reducing ointment generally saturating each of said pads, said ointment comprising tolnaftate, acetone, tocopheryl acetate, propylene glycol, and water, wherein said tolnaftate is between 1% and 2% by volume of the ointment; and a package having an upper layer and a lower layer joined at perimeter edges of the upper and lower layers, said package being segregated into a plurality of discreet packets, a plurality of perforations extending through said package along lines dividing said packets from each other, each of said pads being positioned in one of said packets, each said packets comprising a plastic material.

5. A method of reducing the itch of an insect bite comprising the steps of:

providing a plurality of pads, each of said pads comprising an absorbent material, said absorbent material comprising a cotton material;

saturating each of said pads with an itch reducing ointment, said ointment comprising tolnaftate, acetone, tocopheryl acetate, propylene glycol, and water, wherein said tolnaftate is between 1% and 2% by volume of the ointment;

providing a package having an upper layer and a lower layer joined at perimeter edges of the upper and lower layers, said package being segregated into a plurality of discreet packets, a plurality of perforations extending through said package along lines dividing said packets from each other;

positioning each of said pads in one of said packets; and removing a pad from a package and applying ointment on the removed pad to the insect bite.

* * * * *